United States Patent
Fung et al.

(10) Patent No.: US 9,874,457 B2
(45) Date of Patent: Jan. 23, 2018

(54) ADAPTIVE LIFESTYLE METRIC ESTIMATION

(71) Applicant: MICROSOFT TECHNOLOGY LICENSING, LLC, Redmond, WA (US)

(72) Inventors: Han Yee Mimi Fung, Bellevue, WA (US); Haithem Albadawi, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 615 days.

(21) Appl. No.: 14/292,078

(22) Filed: May 30, 2014

(65) Prior Publication Data

US 2015/0345985 A1   Dec. 3, 2015

(51) Int. Cl.
*A61B 5/11*   (2006.01)
*G01P 15/08*   (2006.01)
(Continued)

(52) U.S. Cl.
CPC ........ *G01C 22/006* (2013.01); *A61B 5/02438* (2013.01); *A61B 5/0531* (2013.01);
(Continued)

(58) Field of Classification Search
None
See application file for complete search history.

(56) References Cited

U.S. PATENT DOCUMENTS 6,097,241 A * 8/2000 Bertin ............... G06F 1/3203
326/31
6,650,942 B2 * 11/2003 Howard ............ A61N 1/378
607/34

(Continued)

FOREIGN PATENT DOCUMENTS

WO   WO 2015/184023 A2 * 12/2015

OTHER PUBLICATIONS

Brage, S. et al., "Hierarchy of Individual Calibration Levels for Heart Rate and Accelerometry to Measure Physical Activity", In Journal of Applied Physiology, vol. 103, Apr. 26, 2007, 11 pages.
(Continued)

*Primary Examiner* — Edward Cosimano
(74) *Attorney, Agent, or Firm* — Alleman Hall Creasman & Tuttle LLP

(57) ABSTRACT

Systems and methods for estimating lifestyle metrics with a wearable electronic device are disclosed herein. One disclosed system may include the wearable electronic device comprising a processor and a sensor system providing inputs to the processor. The sensor system may include a high power sensor and a low power sensor. The processor may operate in a high power mode in which both sensors are operational and a low power mode in which the high power sensor is not operational. In the high power mode, the processor may compute a lifestyle metric about a user for a first time period based on first data from the high power sensor. In the low power mode, the processor may compute the lifestyle metric for a second time period based on second data from the low power sensor and the first data and/or a derivative of the first data.

20 Claims, 4 Drawing Sheets

(51) Int. Cl.
| | |
|---|---|
| G01D 21/00 | (2006.01) |
| G06F 17/40 | (2006.01) |
| G06F 19/00 | (2011.01) |
| G01C 22/00 | (2006.01) |
| G01P 15/02 | (2013.01) |
| G06F 1/32 | (2006.01) |
| G04G 21/02 | (2010.01) |
| A61B 5/024 | (2006.01) |
| A61B 5/053 | (2006.01) |
| G01C 21/16 | (2006.01) |
| G01C 25/00 | (2006.01) |
| A61B 5/00 | (2006.01) |
| A61B 5/01 | (2006.01) |

(52) U.S. Cl.
CPC ............ *A61B 5/1118* (2013.01); *A61B 5/681* (2013.01); *G01C 21/165* (2013.01); *G01C 25/00* (2013.01); *G01P 15/02* (2013.01); *G04G 21/02* (2013.01); *G04G 21/025* (2013.01); *G06F 1/3206* (2013.01); *G06F 19/3406* (2013.01); *G06F 19/3431* (2013.01); *A61B 5/01* (2013.01); *A61B 5/11* (2013.01); *A61B 5/4866* (2013.01); *A61B 5/6898* (2013.01); *A61B 2560/0209* (2013.01); *A61B 2562/0219* (2013.01); *G01D 21/00* (2013.01); *G01P 15/08* (2013.01); *G06F 17/40* (2013.01); *G06F 19/00* (2013.01)

(56) References Cited

U.S. PATENT DOCUMENTS

| | | | |
|---|---|---|---|
| 7,959,567 B2 | 6/2011 | Stivoric et al. | |
| 7,967,731 B2 | 6/2011 | Kil | |
| 8,388,532 B2 | 3/2013 | Morgan | |
| 8,548,770 B2 | 10/2013 | Yuen et al. | |
| 8,579,827 B1 | 11/2013 | Rulkov et al. | |
| 2002/0183801 A1* | 12/2002 | Howard | A61N 1/378 607/34 |
| 2004/0102931 A1 | 5/2004 | Ellis et al. | |
| 2008/0167573 A1 | 7/2008 | Stivoric et al. | |
| 2010/0250179 A1 | 9/2010 | Mariano et al. | |
| 2011/0015467 A1 | 1/2011 | Dothie et al. | |
| 2011/0054359 A1 | 3/2011 | Sazonov et al. | |
| 2011/0098583 A1 | 4/2011 | Pandia et al. | |
| 2012/0047384 A1* | 2/2012 | Morris | G06F 1/263 713/340 |
| 2012/0095622 A1* | 4/2012 | Lynch | B64C 25/00 701/3 |
| 2012/0316406 A1* | 12/2012 | Rahman | G01C 22/006 600/301 |
| 2012/0316455 A1* | 12/2012 | Rahman | G01C 22/006 600/547 |
| 2012/0316456 A1* | 12/2012 | Rahman | G06F 1/163 600/547 |
| 2013/0133427 A1 | 5/2013 | Yudovsky et al. | |
| 2013/0190657 A1 | 7/2013 | Flaction et al. | |
| 2013/0198214 A1 | 8/2013 | Hall | |
| 2013/0211858 A1 | 8/2013 | Ohnemus et al. | |
| 2014/0266780 A1* | 9/2014 | Rahman | G05B 1/01 340/870.02 |
| 2014/0303900 A1* | 10/2014 | Rahman | G05B 1/01 702/19 |
| 2014/0306821 A1* | 10/2014 | Rahman | G05B 1/01 340/539.11 |
| 2015/0135284 A1* | 5/2015 | Bogard | H04L 63/107 726/5 |

OTHER PUBLICATIONS

Cho, D. et al., "AutoGait: A Mobile Platform that Accurately Estimates the Distance Walked", In Proceedings of the 2010 IEEE International Conference on Pervasive Computing and Communications (PerCom), Mar. 29, 2010, 9 pages.

Shahabdeen, J. et al., "Ambulatory Energy Expenditure Estimation: A Machine Learning Approach", In Proceedings of the Twenty-Second Innovative Applications of Artificial Intelligence Conference (IAAI-10), Jul. 11, 2010, 7 pages.

ISA European Patent Office, International Search Report and Written Opinion Issued in Application No. PCT/US2015/032767, Jan. 21, 2016, WIPO, 17 pages.

Fingas, Jon, "TomTom's new GPS watches track your heart rate without a chest strap (update: US pricing)", http://www.engadget.com/2014/04/03/tomtom-cardio-gps-watches/, Apr. 3, 2014, 10 pages.

Goode, Lauren, "Samsung's New Gear Fit Needs to Work on the "Fit" Part", http://recode.net/2014/04/08/samsungs-new-gear-fit-needs-to-work-on-the-fit-part/, Apr. 8, 2014, 10 pages.

"Samsung Gear Fit, Gear 2 and Gear 2 Neo go on sale worldwide", NDTV Gadgets, http://gadgets.ndtv.com/others/news/samsung-gear-fit-gear-2-and-gear-2-neo-go-on-sale-worldwide-507220, Apr. 11, 2014, 3 pages.

Poeter, Damon, "Meet Simband, Samsung's Next-Gen Health Tracker", http://www.pcmag.com/article2/0,2817,2458663,00.asp, May 28, 2014, 5 pages.

Choi, et al., "Ambulatory Stress Monitoring with Minimally-Invasive Wearable Sensors", In Proceedings of Department Computer Science and Engineering, Texas A&M University, Nov. 1, 2010, 8 pages.

IPEA European Patent Office, International Preliminary Report on Patentability issued in PCT Application No. PCT/US2015/032767, dated May 30, 2016, WIPO, 6 pages.

\* cited by examiner

ADAPTIVE LIFESTYLE METRIC ESTIMATION

DETAILED DESCRIPTION

In the pursuit of a healthy lifestyle, many people may find it beneficial to track various lifestyle metrics such as calories expended, distance traveled, hydration levels, etc. This often may involve sensors collecting data and a device to calculate an estimation of the lifestyle metric based on the sensor data. The lifestyle metric may be tracked continuously or only for a short period of time, such as during exercise. While such lifestyle metrics provide powerful information to the user, outfitting sensors to the human body to track such lifestyle metrics presents many challenges. One such challenge is that operating sensors to measure lifestyle metrics consumes power and may shorten battery life.

Systems for estimating lifestyle metrics with a wearable electronic device may include a wearable electronic device comprising a processor and a sensor system providing inputs to the processor. The sensor system may include a high power sensor that consumes a greater amount of power when in operation than a low power sensor. The processor may be configured to operate in a high power mode in which both sensors are operational and a low power mode in which the low power sensor is operational and the high power sensor is not operational. In the high power mode, the processor may be configured to compute a lifestyle metric about a user for a first time period based on first data from the high power sensor. In the low power mode, the processor may be configured to compute the lifestyle metric for a second time period based on second data from the low power sensor and the first data and/or a derivative of the first data.

Figure 1A:
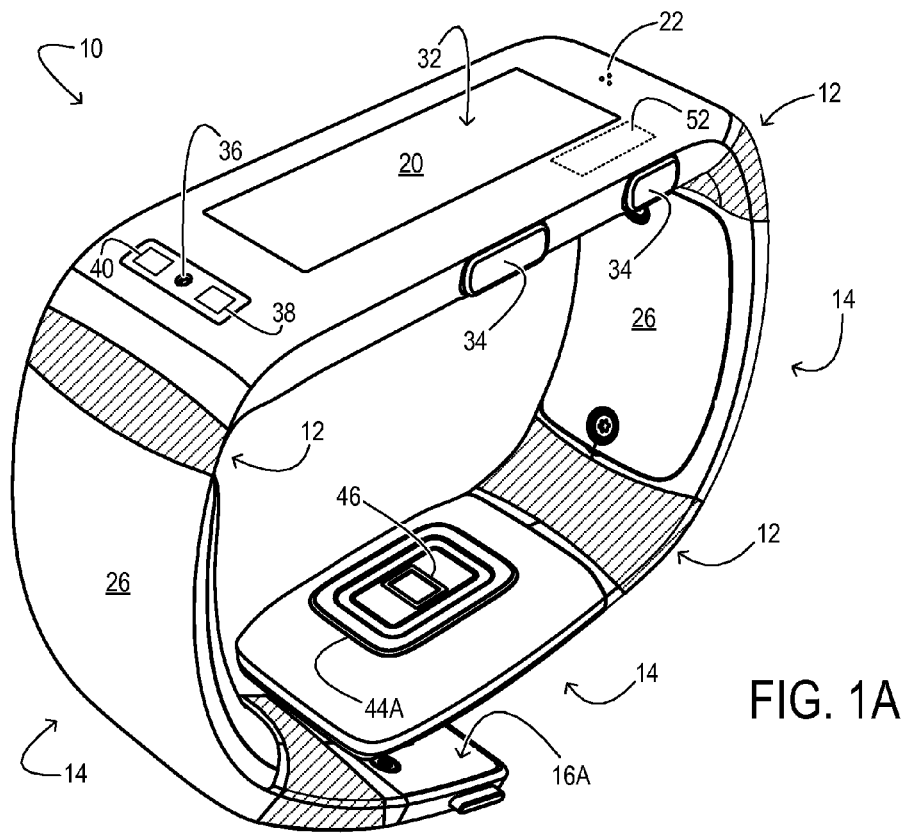
FIGS. 1A and 1B show an example sensory-and-logic system in the form of a wearable electronic device.
Figure 1B:
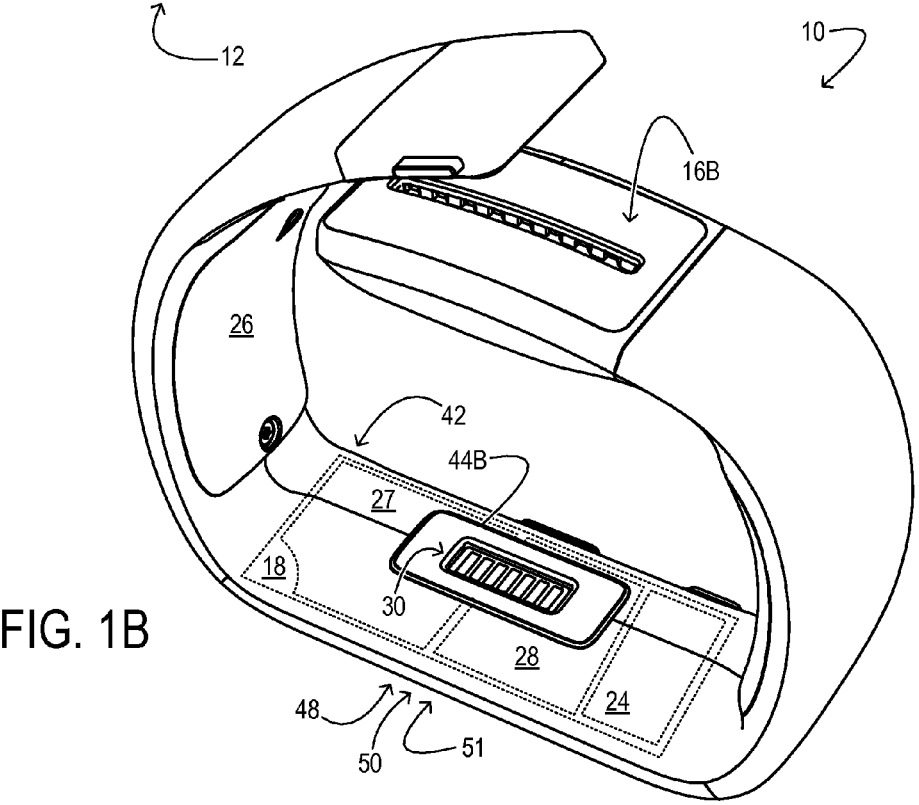

FIGS. 1A and 1B show aspects of an example sensory-and-logic system in the form of a wearable electronic device 10. The illustrated device is band-shaped and may be worn around a wrist. Device 10 includes at least four flexion regions 12 linking less flexible regions 14. The flexion regions of device 10 may be elastomeric in some examples. Fastening componentry 16A and 16B is arranged at both ends of the device. The flexion regions and fastening componentry enable the device to be closed into a loop and to be worn on a user's wrist. In other implementations, wearable electronic devices of a more elongate band shape may be worn around the user's bicep, waist, chest, ankle, leg, head, or other body part. The device, for example, may take the form of eye glasses, a head band, an arm-band, an ankle band, a chest strap. In another implementation, the device may be an implantable device to be implanted in tissue.

Wearable electronic device 10 includes various functional components integrated into regions 14. In particular, the electronic device includes a compute system 18, display 20, loudspeaker 22, communication suite 24, and various sensors. These components draw power from one or more energy-storage cells 26. A battery—e.g., a lithium ion battery—is one type of energy-storage cell suitable for this purpose. Examples of alternative energy-storage cells include super- and ultra-capacitors. In devices worn on the user's wrist, the energy-storage cells may be curved to fit the wrist, as shown in the drawings.

In general, energy-storage cells 26 may be replaceable and/or rechargeable. In some examples, recharge power may be provided through a universal serial bus (USB) port 30, which includes a magnetic latch to releasably secure a complementary USB connector. In other examples, the energy storage cells may be recharged by wireless inductive or ambient-light charging. In still other examples, the wearable electronic device may include electro-mechanical componentry to recharge the energy storage cells from the user's adventitious or purposeful body motion. For example, batteries or capacitors may be charged via an electromechanical generator integrated into device 10. The generator may be turned by a mechanical armature that turns while the user is moving and wearing device 10.

In wearable electronic device 10, compute system 18 is situated below display 20 and operatively coupled to the display, along with loudspeaker 22, communication suite 24, and the various sensors. The compute system includes a data-storage machine 27 to hold data and instructions, and a logic machine 28 to execute the instructions. Aspects of the compute system are described in further detail with reference to FIG. 4.

Display 20 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, LCOS array) may be frontlit via ambient light. A curved display may also be used. Further, AMOLED displays or quantum dot displays may be used.

Communication suite 24 may include any appropriate wired or wireless communications componentry. In FIGS. 1A and 1B, the communications suite includes USB port 30, which may be used for exchanging data between wearable electronic device 10 and other computer systems, as well as providing recharge power. The communication suite may further include two-way BLUETOOTH (wireless communication protocol), WI-FI (wireless local area network), cellular, near-field communication and/or other radios. In some implementations, the communication suite may include an additional transceiver for optical, line-of-sight (e.g., infrared) communication.

In wearable electronic device 10, touch-screen sensor 32 is coupled to display 20 and configured to receive touch input from the user. The touch sensor may be resistive, capacitive, or optically based. Pushbutton sensors may be used to detect the state of push buttons 34, which may include rockers. Input from the pushbutton sensors may be used to enact a home-key or on-off feature, control audio volume, turn the microphone on or off, etc.

FIGS. 1A and 1B show various other sensors of wearable electronic device 10. Such sensors include microphone 36, visible-light sensor 38, ultraviolet sensor 40, and ambient temperature sensor 42. The microphone provides input to compute system 18 that may be used to measure the ambient sound level or receive voice commands from the wearer. Input from the visible-light sensor, ultraviolet sensor, and ambient temperature sensor may be used to assess aspects of the wearer's environment—i.e., the temperature, overall lighting level, and whether the wearer is indoors or outdoors.

FIGS. 1A and 1B show a pair of contact sensor modules 44A and 44B, which contact the wearer's skin when wearable electronic device 10 is worn. The contact sensor modules may include independent or cooperating sensor elements, to provide a plurality of sensory functions. For example, the contact sensor modules may provide an electrical resistance and/or capacitance sensory function, which measures the electrical resistance and/or capacitance of the wearer's skin. Compute system 18 may use such input to assess whether or not the device is being worn, for instance. In some implementations, the sensory function may be used to determine how tightly the wearable electronic device is being worn. In the illustrated configuration, the separation between the two contact-sensor modules provides a relatively long electrical path length, for more accurate measurement of skin resistance. In some examples, a contact sensor module may also provide measurement of the wearer's skin temperature. Arranged inside contact sensor module 44A in the illustrated configuration is an optical pulse rate sensor 46. The optical pulse-rate sensor may include an LED emitter and matched photodiode to detect blood flow through the capillaries in the skin and thereby provide a measurement of the wearer's pulse rate.

Wearable electronic device 10 may also include motion sensing componentry, such as an accelerometer 48, gyroscope 50, and magnetometer 51. The accelerometer and gyroscope may furnish inertial and/or rotation rate data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation. The wearable electronic device may also include a global positioning system (GPS) receiver 52 for determining the wearer's geographic location and/or velocity. In some configurations, the antenna of the GPS receiver may be relatively flexible and extend into flexion regions 12.

Compute system 18, via the sensory functions described herein, is configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable electronic device, and only non-personal, summary data transmitted to the remote system.

Figure 2B:
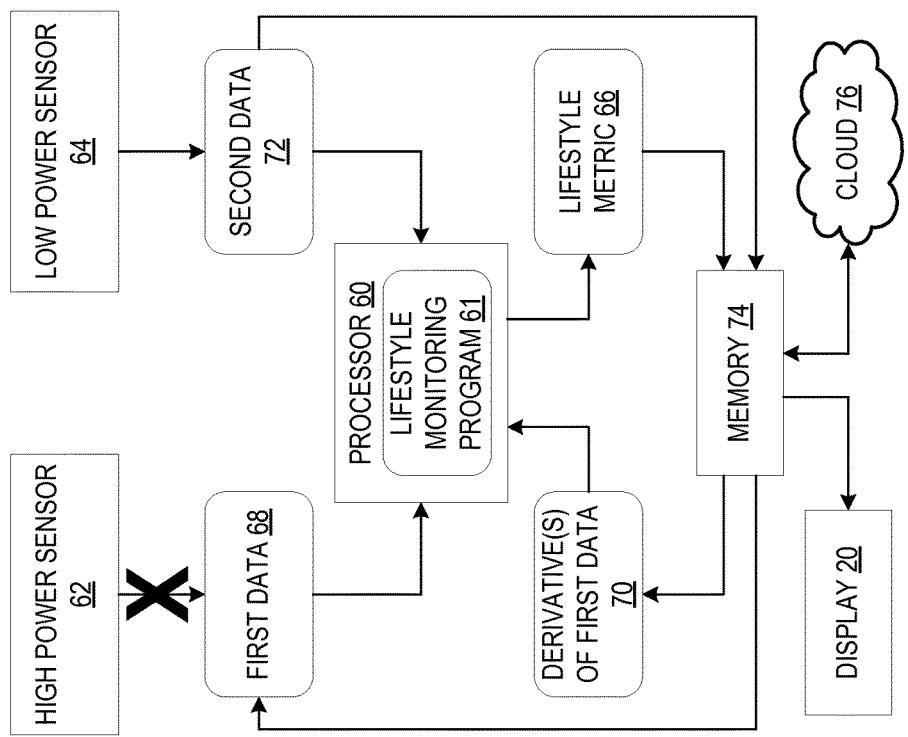
FIGS. 2A and 2B show the operation of a lifestyle monitoring program of the wearable electronic device in a high power mode and a low power mode.
Figure 2A:
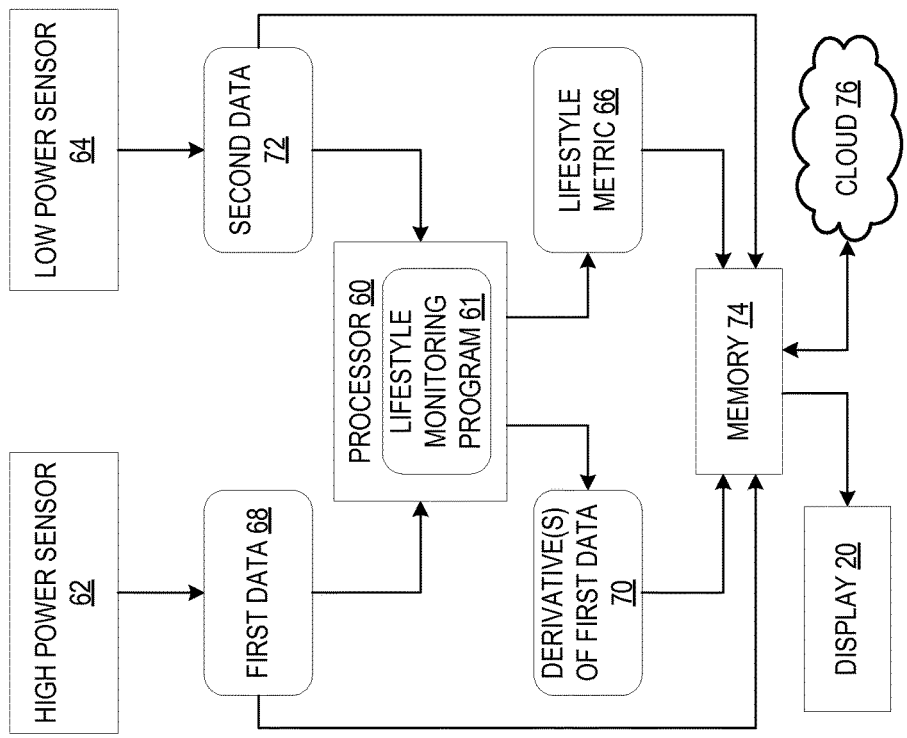

FIGS. 2A and 2B show an operation of a lifestyle monitoring program 61 on the wearable electronic device 10 in a high power mode and a low power mode, respectively. The wearable electronic device 10 may comprise a processor 60, for example of logic machine 28, and a sensor system providing inputs to the processor 60 via the lifestyle monitoring program 61. The sensor system may be the sensor suite 412 described below with reference to FIG. 4 and may include at least a first sensor and a second sensor of the various other sensors described above, for example. The first sensor may be a high power sensor 62 that consumes a greater amount of power when in operation than the second sensor, which may be a low power sensor 64.

The processor 60 may be configured to operate the lifestyle monitoring program 61 in a high power mode in which both sensors 62 and 64 are operational and a low power mode in which the low power sensor 64 is operational and the high power sensor 62 is not operational. Accordingly, the high power sensor 62 may be intermittently available while the low power sensor 64 is continuously operated. Because other sensors and components of the wearable electronic device 10 may be running during one or both modes, a power disparity between modes of the entire device may not be the same as that between just the high and low power sensors 62 and 64. Furthermore, regardless of the relative power consumption of the high and low power sensors 62 and 64, more power may be consumed in the high power mode than in the low power mode because other than the high power sensor 62, the same sensors in operation during the low power mode may also be in operation during the high power mode, including the low power sensor 64.

The processor 60 may switch between modes in response to a signal from a sensor or for various other reasons. For example, modes may be switched if the high power sensor 62 is not sensing properly or returns to proper operation after not sensing properly. The modes may also be manually switched, for instance by a user interacting with the GUI or push buttons 34. As one example, the user may wish to begin a workout and track one or more lifestyle metrics more closely than during the rest of the day when the user is relatively inactive.

In the high power mode illustrated in FIG. 2A, the processor 60 may be configured to execute the lifestyle monitoring program 61 to compute a lifestyle metric 66 about the user for a first time period based on first data 68 from the high power sensor 62. The first data 68 may be used to calculate a derivative 70 of the first data 68. Note that the term "derivative" may be used to mean a value or function derived in any manner from data and is not limited to a value or function derived by differential calculus, although a differential calculus derivation is intended to fall within the scope of the word "derivative" as used herein.

In the low power mode illustrated in FIG. 2B, the processor 60 may be configured to compute the lifestyle metric 66 for a second time period based on second data 72 from the low power sensor 64 and the first data 68 and/or the derivative 70 of the first data 68. In both modes, the first data 68, the derivative 70 of the first data 68, the lifestyle metric 66, and/or second data 72, if available, may be stored in or retrieved from memory 74 of the data-storage machine 28, displayed on display 20, or sent to or retrieved from a cloud 76. For example, in the low power mode, the first data 68 collected during the high power mode and/or derivative 70 of the first data 68 may be retrieved from the memory 74 and used when computing the lifestyle metric 66 for the second time period.

The wearable electronic device 10 may comprise a band wearable on a wrist of the user. The band may be formed at least partially by the flexion regions 12 linking the less flexible regions 14, for example. As described above, the wearable electronic device 10 may alternatively be wearable on other body parts of the user.

In one implementation, the high power sensor 62 may be the global positioning system (GPS) receiver 52 and the low power sensor 64 may be the accelerometer 48. The lifestyle metric 66 may then be a distance traveled by the user and the derivative 70 of the first data 68 may be a stride length of the user. The stride length may be calculated simply by dividing the distance traveled by the user as measured by the GPS receiver 52 (from the first data 68) by a number of steps taken as measured by the accelerometer 48 (from the second data 72). In the low power mode, if no stride length is previously recorded, the stride length may be estimated using the physical profile of the user, e.g. age, sex, weight, and/or height. However, a more accurate distance may be estimated by using the stride length derived from the first data 68, even when the GPS receiver 52 is currently not in operation. In this manner, the lifestyle metric 66 may be estimated based on the individual user rather than average users.

The processor 60 may be further configured to sum the lifestyle metric 66 and a previous total lifestyle metric to obtain a current total lifestyle metric. For example, the processor 60 may be further configured to sum the distance traveled by the user and a previous total distance to obtain a current total distance. The current total distance may include distances measured during the high and/or low power modes. If the user wishes to accurately track his movement throughout the day, the different modes of the wearable electronic device 10 may allow him to do so without unduly draining the battery or losing accuracy.

The stride length may be one of a plurality of stride lengths, each respective stride length being calculated for an associated gait of the user. For instance, once the lifestyle monitoring program 61 determines that a GPS signal is strong and has minimal error, the lifestyle monitoring program 61 may be configured to calculate the stride length while the user is walking, jogging, or sprinting, and save any of these stride lengths in the memory 74. Three gaits are given as an example but any reasonable number of gaits may be used. Each of the stride lengths may replace an estimated stride length based on the user's physical profile, and the lifestyle monitoring program 61 may be configured to verify that the calculated stride lengths are within a tolerance of the estimated stride lengths based on the user's profile. Then, when the lifestyle monitoring program 61 is operating in the low power mode, the stride length corresponding to the user's current movement pattern as detected by the accelerometer 48 or another sensor may be used to better estimate the distance traveled by the user.

One potential benefit of operating in the low and high power modes may include lowering power consumption of the wearable electronic device 10. However, this configuration is not limited to this motivation. There may be times the high power sensor 62 is unavailable or useless for the situation at hand. For example, the GPS receiver 52 may not have a strong signal due to, for instance, the user walking in an underground parking garage. The GPS receiver 52 also may not provide useable first data 68 if the user is running on a treadmill in one location, for example. In both cases, if previously collected first data 68 is available, it may be advantageous to operate in the low power mode and continue to calculate the lifestyle metric 66.

In another implementation, the high power sensor 62 may be a heart rate sensor and the low power sensor 64 may be the accelerometer 48. The heart rate sensor may be optical pulse rate sensor 46, for example, but may also be any other type of heart rate sensor. The lifestyle metric 66 may then be a calorie expenditure. As with the distance traveled in the above implementation, the calorie expenditure may be summed with a previous total calorie expenditure to obtain a current total calorie expenditure. The current total calorie expenditure may include calorie expenditures measured during the high and/or low power modes. If the user wishes to accurately track his energy burned throughout the day, the different modes of the wearable electronic device 10 may allow him to do so without unduly draining the battery or losing accuracy.

The derivative 70 of the first data 68 may comprise a first derivative and a second derivative, the first derivative being a resting heart rate and the second derivative being a recovery rate. The resting heart rate or basal heart rate may typically be a low heart rate measured while the user is relaxed. A value for the resting heart rate may initially be inputted by the user before a more accurate value is derived.

The processor 60 may be further configured to compute the resting heart rate by collecting the first data 68 while the user is sleeping, filtering out first data 68 outside a heart rate range, and computing the resting heart rate based on the filtered first data 68. The heart rate range may be 35-85 BPM, as one example. In this manner, the resting heart rate may be more accurately estimated based on the individual user rather than average users. Without such prior or derived data, the lifestyle monitoring program 61 may base calculations on the user profile data, which may include user inputted values, and estimate a less accurate heart rate and calorie expenditure.

The recovery rate may typically be a drop in heart rate, usually measured in beats per minute (bpm), from a time soon after exercise until the heart rate reaches a lower heart rate. More specifically, the lower heart rate may be the resting heart rate, or the time from soon after exercise until the lower heart rate is reached may be a set interval, for instance, two minutes. Both the extent of the drop in heart rate and the amount of time over which the heart rate drops may be incorporated into the recovery rate. For example, the user may go for a run and experience a reduction in heart rate afterward of 20 bpm over one minute. Obtaining an accurate resting heart rate and recovery rate may enable the lifestyle monitoring program 61 to more accurately estimate a current heart rate in the absence of real-time first data 68 from the heart rate sensor, and from the estimated heart rate, calculate a more accurate estimate of calorie expenditure. For instance, if the user exercises and then stops, the recovery rate may determine a smooth and accurate drop in heart rate rather than assuming a sudden change or an average user, avoiding under- or overestimating the calorie expenditure.

Once derived, derivatives 70 of the first data 68 may replace estimations based on user inputted values, or even previous derivatives 70. The values may be inputted during an initial setup phase of the wearable electronic device 10, for example. The user may become more or less fit over time, change environments, become injured, age, or otherwise deviate from the derivative 70 such that calculations based on the derivative 70 saved in the memory 74 are no longer accurate. Likewise, data such as the first data 68, second data 72, and the lifestyle metric 66 may also be updated in the memory 74 over time. In this way, the lifestyle monitoring program 61 may adapt to changing user conditions over time.

The processor 60 may be further configured to operate the lifestyle monitoring program 61 in a remote mode in which the high power sensor 62 is a remote high power sensor in a remote device connected by the cloud 76. The processor 60 may be configured to receive the first data 68 as remote data from the remote high power sensor and compute the lifestyle metric 66 based on the remote data. For example, the remote device may be a smartphone in the user's hand or pocket. In such a configuration, the wearable electronic device 10 may perform the same operations as in the high power mode by receiving remote data from the remote device over BLUETOOTH (wireless communication protocol) or WI-FI (wireless local area network), for example, without powering the high power sensor 62 itself.

Figure 3:
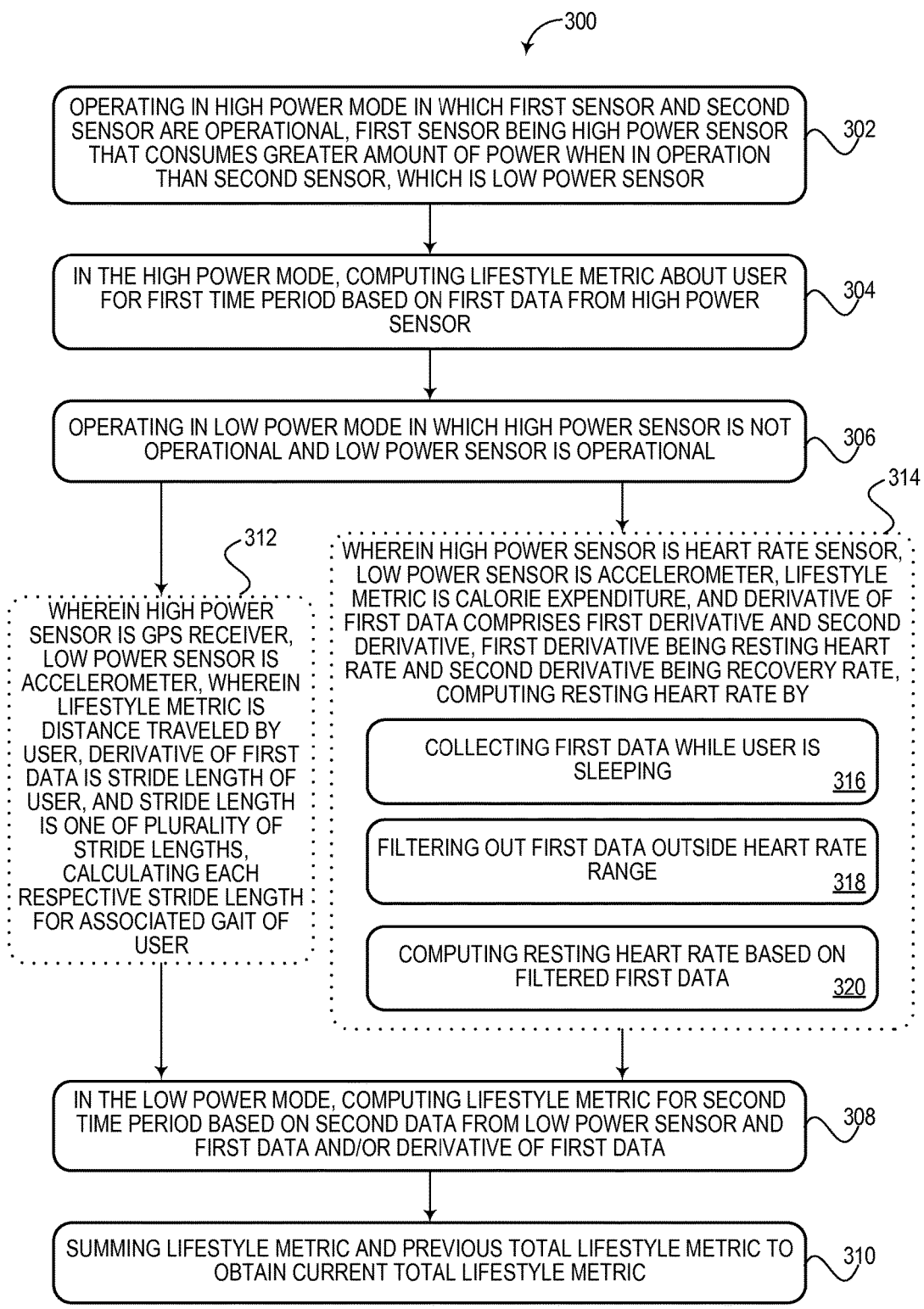
FIG. 3 is a flowchart of a method for estimating lifestyle metrics with a wearable electronic device.

FIG. 3 is a flowchart of a method 300 for estimating lifestyle metrics with a lifestyle monitoring program on a wearable electronic device. The following description of method 300 is provided with reference to the software and hardware components of the wearable electronic device described above and shown in FIGS. 1A, 1B, 2A, 2B, and 4. It will be appreciated that method 300 may also be performed in other contexts using other suitable hardware and software components.

With reference to FIG. 3, at 302 the method 300 may include operating in a high power mode in which a first sensor and a second sensor are operational, the first sensor being a high power sensor that consumes a greater amount of power when in operation than the second sensor, which is a low power sensor.

At 304 the method 300 may include, in the high power mode, computing a lifestyle metric about a user for a first time period based on first data from the high power sensor. At 306 the method 300 may include operating in a low power mode in which the high power sensor is not operational and the low power sensor is operational. By the wearable electronic device switching between the two modes, the low power sensor may be continuously operated while the high power sensor is intermittently available. Operating in the low power mode at least part of the time may save battery power without an accompanying unacceptable drop in accuracy.

The first data may be used to calculate a derivative of the first data. At 308 the method 300 may include, in the low power mode, computing the lifestyle metric for a second time period based on second data from the low power sensor and the first data and/or a derivative of the first data. In both modes, the first data, the derivative of the first data, the lifestyle metric, and/or second data, if available, may be stored in or retrieved from memory, displayed on a display, or sent to or retrieved from a cloud. For example, in the low power mode, the first data collected during the high power mode and/or derivative of the first data may be retrieved from the memory and used when computing the lifestyle metric for the second time period.

At 310 the method 300 may include summing the lifestyle metric and a previous total lifestyle metric to obtain a current total lifestyle metric. If the user wishes to accurately track her body's condition and movement throughout the day, the different modes of the wearable electronic device may allow her to do so without unduly draining the battery or losing accuracy. As mentioned above, the wearable electronic device may comprise a band wearable on a wrist of the user. The band may be formed at least partially by flexion regions linking less flexible regions, for example, and may allow the user to wear the wearable electronic device and collect data throughout the day.

In one implementation of the method 300, the high power sensor may be a global positioning system (GPS) receiver and the low power sensor may be an accelerometer. The lifestyle metric may be a distance traveled by the user and the derivative of the first data may be a stride length of the user. In such an implementation, at 310 the method 300 may then include summing the distance traveled by the user and a previous total distance to obtain a current total distance. At 312 the method 300 may include the stride length being one of a plurality of stride lengths, each respective stride length being calculated for an associated gait of the user. The stride length may be calculated as above.

Alternatively, in another implementation of the method 300, the high power sensor may be a heart rate sensor and the low power sensor may be an accelerometer. The lifestyle metric may be a calorie expenditure and the derivative of the first data may comprise a first derivative and a second derivative. The first derivative may be a resting heart rate and the second derivative may be a recovery rate. A value for the resting heart rate may initially be inputted by the user before a more accurate value is derived.

At 314 the method 300 may include computing the resting heart rate. The resting heart rate may be computed by collecting the first data while the user is sleeping (316), filtering out first data outside a heart rate range (318), and computing the resting heart rate based on the filtered first data (320). In this manner, the resting heart rate may be more accurately estimated based on the individual user rather than average users. Without such prior or derived data, the lifestyle monitoring program may base calculations on the user profile data, which may include user inputted values, and estimate a less accurate heart rate and calorie expenditure. The recovery rate may typically be defined as above.

The above described systems and methods may be used to adaptively calculate an estimation of lifestyle metrics of a user such as calories expended and distance traveled. The systems and methods may include a high power mode and a low power mode in which various sensors are or are not in operation. This approach may have the potential advantages of improving energy consumption in a wearable electronic device, possibly leading to extended battery life or operation time of the device.

As evident from the foregoing description, the methods and processes described herein may be tied to a sensory-and-logic system of one or more machines. Such methods and processes may be implemented as a computer-application program or service, an application-programming interface (API), a library, firmware, and/or other computer-program product. FIGS. 1A and 1B show one, non-limiting example of a sensory-and-logic system to enact the methods and processes described herein. However, these methods and process may also be enacted on sensory-and-logic systems of other configurations and form factors, as shown schematically in FIG. 4.

Figure 4:
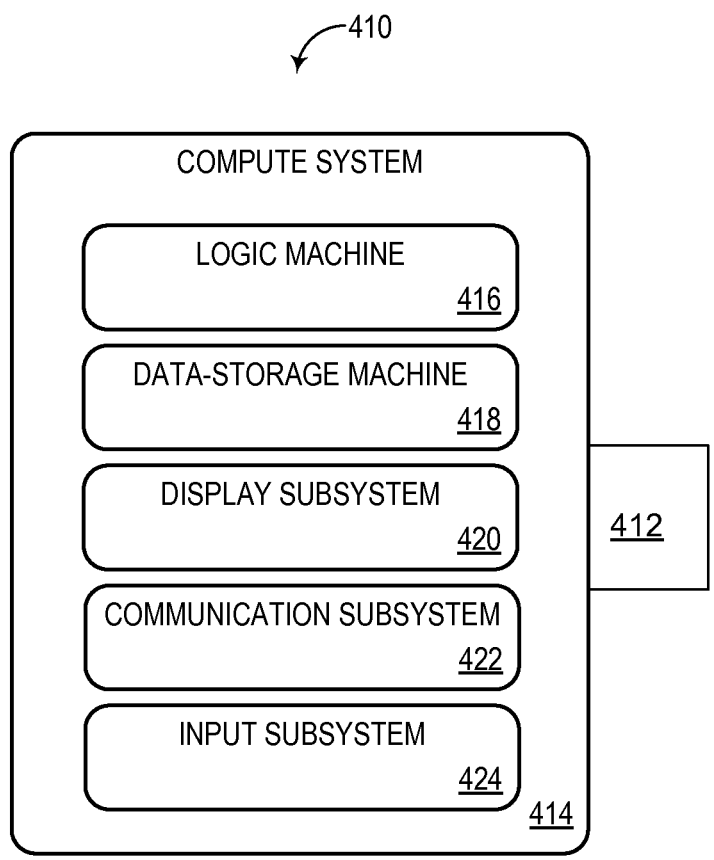
FIG. 4 shows a simplified schematic view of the sensory-and-logic system.

FIG. 4 schematically shows a form-agnostic sensory-and-logic system 410 that includes a sensor suite 412 operatively coupled to a compute system 414. The compute system includes a logic machine 416 and a data-storage machine 418. The compute system is operatively coupled to a display subsystem 420, a communication subsystem 422, an input subsystem 424, and/or other components not shown in FIG. 4.

Logic machine 416 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 416 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 418 includes one or more physical devices configured to hold instructions executable by logic machine 416 to implement the methods and processes described herein. When such methods and processes are implemented, the state of the data-storage machine may be transformed—e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

It will be appreciated that data-storage machine 418 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 416 and data-storage machine 418 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 420 may be used to present a visual representation of data held by data-storage machine 418. This visual representation may take the form of a graphical user interface (GUI). As the herein described methods and processes change the data held by the storage machine, and thus transform the state of the storage machine, the state of display subsystem 420 may likewise be transformed to visually represent changes in the underlying data. Display subsystem 420 may include one or more display subsystem devices utilizing virtually any type of technology. Such display subsystem devices may be combined with logic machine 416 and/or data-storage machine 418 in a shared enclosure, or such display subsystem devices may be peripheral display subsystem devices. Display 20 of FIGS. 1A and 1B is an example of display subsystem 420.

Communication subsystem 422 may be configured to communicatively couple compute system 414 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 24 of FIGS. 1A and 1B is an example of communication subsystem 422.

Input subsystem 424 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. Touch-screen sensor 32 and push buttons 34 of FIGS. 1A and 1B are examples of input subsystem 424.

Sensor suite 412 may include one or more different sensors—e.g., a touch-screen sensor, push-button sensor, microphone, visible-light sensor, ultraviolet sensor, ambient-temperature sensor, contact sensors, optical pulse-rate sensor, accelerometer, gyroscope, magnetometer, and/or GPS receiver—as described above with reference to FIGS. 1A and 1B.

It will be understood that the configurations and approaches described herein are exemplary in nature, and that these specific implementations or examples are not to be taken in a limiting sense, because numerous variations are feasible. The specific routines or methods described herein may represent one or more processing strategies. As such, various acts shown or described may be performed in the sequence shown or described, in other sequences, in parallel, or omitted.

The subject matter of this disclosure includes all novel and non-obvious combinations and sub-combinations of the various processes, systems and configurations, and other features, functions, acts, and/or properties disclosed herein, as well as any and all equivalents thereof.

What is claimed is:

1. A wearable electronic device switchable between power modes in response to a user interaction with the device or a signal from a sensor of the device, the device comprising:
   a processor; and
   a sensor system providing inputs to the processor, the sensor system including a first sensor and a second sensor, the first sensor being a high power sensor that consumes a greater amount of power when in operation than the second sensor, which is a low power sensor;
   wherein the processor is configured to operate in a high power mode in which both sensors are operational and a low power mode in which the low power sensor is operational and the high power sensor is not operational;
   wherein, in the high power mode, the processor is configured to compute a lifestyle metric about a user for a first time period based on first data from the high power sensor; and
   wherein, in the low power mode, the processor is configured to compute the lifestyle metric for a second time period based on:
      second data from the low power sensor; and
      the first data and/or a derivative of the first data.

2. The wearable electronic device of claim 1, further comprising a band wearable on a wrist of the user.

3. The wearable electronic device of claim 1, wherein the high power sensor is a global positioning system (GPS) receiver and the low power sensor is an accelerometer.

4. The wearable electronic device of claim 3, wherein the lifestyle metric is a distance traveled by the user and the derivative of the first data is a stride length of the user.

5. The wearable electronic device of claim 4, wherein the processor is further configured to sum the distance traveled by the user and a previous total distance to obtain a current total distance.

6. The wearable electronic device of claim 4, wherein the stride length is one of a plurality of stride lengths, each respective stride length being calculated for an associated gait of the user.

7. The wearable electronic device of claim 1, wherein the high power sensor is a heart rate sensor and the low power sensor is an accelerometer.

8. The wearable electronic device of claim 7, wherein the lifestyle metric is a calorie expenditure and the derivative of the first data comprises a first derivative and a second derivative, the first derivative being a resting heart rate and the second derivative being a recovery rate.

9. The wearable electronic device of claim 8, wherein the processor is further configured to compute the resting heart rate by:
   collecting the first data while the user is sleeping;
   filtering out first data outside a heart rate range; and
   computing the resting heart rate based on the filtered first data.

10. The wearable electronic device of claim 8, wherein the processor is further configured to operate in a remote mode in which the high power sensor is a remote high power sensor in a remote device, wherein the processor is configured to:
   receive remote data from the remote high power sensor; and
   compute the lifestyle metric based on the remote data.

11. A method for estimating lifestyle metrics with a wearable electronic device switchable between power modes in response to a user interaction with the device or a signal from a sensor of the device, the method comprising:
   operating in a high power mode in which a first sensor and a second sensor are operational, the first sensor being a high power sensor that consumes a greater amount of power when in operation than the second sensor, which is a low power sensor;
   in the high power mode, computing a lifestyle metric about a user for a first time period based on first data from the high power sensor;
   operating in a low power mode in which the high power sensor is not operational and the low power sensor is operational; and
   in the low power mode, computing the lifestyle metric for a second time period based on:
     second data from the low power sensor; and
     the first data and/or a derivative of the first data.

12. The method of claim 11, wherein the wearable electronic device further comprises a band wearable on a wrist of the user.

13. The method of claim 11, wherein the high power sensor is a heart rate sensor and the low power sensor is an accelerometer.

14. The method of claim 13, wherein the lifestyle metric is a calorie expenditure and the derivative of the first data comprises a first derivative and a second derivative, the first derivative being a resting heart rate and the second derivative being a recovery rate.

15. The method of claim 14, further comprising computing the resting heart rate by:
   collecting the first data while the user is sleeping;
   filtering out first data outside a heart rate range; and
   computing the resting heart rate based on the filtered first data.

16. The method of claim 11, wherein the high power sensor is a global positioning system (GPS) receiver and the low power sensor is an accelerometer.

17. The method of claim 16, wherein the lifestyle metric is a distance traveled by the user and the derivative of the first data is a stride length of the user.

18. The method of claim 17, further comprising summing the distance traveled by the user and a previous total distance to obtain a current total distance.

19. The method of claim 17, wherein the stride length is one of a plurality of stride lengths, each respective stride length being calculated for an associated gait of the user.

20. A wearable electronic device switchable between power modes in response to a user interaction with the device or a signal from a sensor of the device, the device comprising:
   a processor;
   a sensor system providing inputs to the processor, the sensor system including a first sensor and a second sensor, the first sensor being a high power sensor that consumes a greater amount of power when in operation than the second sensor, which is a low power sensor, wherein the high power sensor is a global positioning system (GPS) receiver and the low power sensor is an accelerometer; and
   a band wearable on a wrist of a user;
   wherein the processor is configured to operate in a high power mode in which both sensors are operational and a low power mode in which the low power sensor is operational and the high power sensor is not operational; wherein
   in the high power mode, the processor is configured to compute a lifestyle metric about the user for a first time period based on first data from the high power sensor; and
   in the low power mode, the processor is configured to compute the lifestyle metric for a second time period based on:
     second data from the low power sensor; and
     the first data and/or a derivative of the first data.

* * * * *